United States Patent  (10) Patent No.: US 11,961,228 B2
Aoyama  (45) Date of Patent: Apr. 16, 2024

(54) MEDICAL IMAGE PROCESSING SYSTEM

(71) Applicant: FUJIFILM Corporation, Tokyo (JP)

(72) Inventor: Tatsuya Aoyama, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 440 days.

(21) Appl. No.: 17/245,895

(22) Filed: Apr. 30, 2021

(65) Prior Publication Data

US 2021/0264592 A1 Aug. 26, 2021

Related U.S. Application Data

(63) Continuation of application No. PCT/JP2019/043027, filed on Nov. 1, 2019.

(30) Foreign Application Priority Data

Nov. 14, 2018 (JP) ................. 2018-213697

(51) Int. Cl.
G06K 9/00 (2022.01)
A61B 5/00 (2006.01)
(Continued)

(52) U.S. Cl.
CPC ........ *G06T 7/0012* (2013.01); *A61B 5/02007* (2013.01); *A61B 5/4842* (2013.01);
(Continued)

(58) Field of Classification Search
CPC .............. G06T 7/0012; G06T 7/11; G06T 2207/10068; G06T 2207/30096;
(Continued)

(56) References Cited

U.S. PATENT DOCUMENTS 9,773,185 B2 * 9/2017 Kanda .................... G06V 20/47
2007/0135715 A1 6/2007 Inoue et al.
(Continued)

FOREIGN PATENT DOCUMENTS

CN 101166456 A 4/2008
CN 101981582 A 2/2011
(Continued)

OTHER PUBLICATIONS

The extended European search report issued by the European Patent Office dated Nov. 11, 2021, which corresponds to European Patent Application No. 19884644.6-1126 and is related to U.S. Appl. No. 17/245,895.
(Continued)

*Primary Examiner* — Dhaval V Patel
(74) *Attorney, Agent, or Firm* — Studebaker & Brackett PC

(57) ABSTRACT

A medical image acquisition unit acquires a medical image obtained by imaging an observation target. A feature amount calculation unit calculates a feature amount of the observation target for each pixel of an image region of the medical image or for each divided region obtained by dividing the image region of the medical image into a specific size. A stage determination unit calculates a distribution index value which is an index value of the spatial distribution of the feature amount of each divided region, and determines the disease stage of the observation target based on the distribution index value.

12 Claims, 9 Drawing Sheets

(51) Int. Cl.
*A61B 5/02* (2006.01)
*G06T 7/00* (2017.01)
*G06T 7/11* (2017.01)
*G06V 10/143* (2022.01)
*G06V 10/25* (2022.01)
*G06V 10/75* (2022.01)
*G06V 10/764* (2022.01)

(52) U.S. Cl.
CPC .............. *G06T 7/11* (2017.01); *G06V 10/143* (2022.01); *G06V 10/25* (2022.01); *G06V 10/751* (2022.01); *G06V 10/764* (2022.01); *G06T 2207/10068* (2013.01); *G06T 2207/30096* (2013.01); *G06T 2207/30101* (2013.01)

(58) Field of Classification Search
CPC . G06T 2207/30101; G06T 2207/10024; G06T 2207/20021; A61B 5/02007; A61B 5/4842; A61B 1/000094; A61B 2576/02; A61B 5/0077; A61B 5/0086; G06V 10/143; G06V 10/25; G06V 10/751; G06V 10/764; G06V 2201/03; G16H 30/40; G16H 50/20
See application file for complete search history.

(56) References Cited

U.S. PATENT DOCUMENTS

| | | | |
|---|---|---|---|
| 2011/0019920 A1 | 1/2011 | Hu | |
| 2013/0051641 A1 | 2/2013 | Tanaka et al. | |
| 2015/0181185 A1 | 6/2015 | Ikemoto et al. | |
| 2016/0089011 A1 | 3/2016 | Shiraishi et al. | |
| 2016/0174886 A1 | 6/2016 | Shiraishi | |
| 2016/0306936 A1* | 10/2016 | Mizobe | G16H 10/60 |
| 2016/0335394 A1* | 11/2016 | Kawagishi | G16H 40/63 |
| 2017/0004625 A1 | 1/2017 | Kamiyama et al. | |
| 2017/0213347 A1* | 7/2017 | Sakaue | G06T 7/0012 |
| 2018/0211385 A1 | 7/2018 | Mai | |
| 2018/0214005 A1 | 8/2018 | Ebata | |
| 2018/0218499 A1 | 8/2018 | Kamon | |

FOREIGN PATENT DOCUMENTS

| | | | | |
|---|---|---|---|---|
| CN | 103327883 A | | 9/2013 | |
| EP | 3 357 406 A1 | | 8/2018 | |
| JP | 2006-166939 A | | 6/2006 | |
| JP | 2006-334115 A | | 12/2006 | |
| JP | 2007-236956 A | | 9/2007 | |
| JP | 2007236956 A | * | 9/2007 | ........... A61B 1/0009 |
| JP | 2014-018333 A | | 2/2014 | |
| JP | 2014018333 A | * | 2/2014 | ......... A61B 1/00009 |
| JP | 2015-085152 A | | 5/2015 | |
| JP | 2016-067778 A | | 5/2016 | |
| WO | 2015/141692 A1 | | 9/2015 | |
| WO | 2017/057414 A1 | | 4/2017 | |
| WO | 2017/057573 A1 | | 4/2017 | |
| WO | 2017/057574 A1 | | 4/2017 | |
| WO | WO-2017057414 A1 | * | 4/2017 | ............... A61B 1/00 |

OTHER PUBLICATIONS

An Office Action; "Notice of Reasons for Refusal", mailed by the Japanese Patent Office dated Apr. 5, 2022, which corresponds to Japanese Patent Application No. 2020-556041 and is related to U.S. Appl. No. 17/245,895; with English language translation.
An Office Action; "Notice of Reasons for Refusal," mailed by the Japanese Patent Office dated Aug. 23, 2022, which corresponds to Japanese Patent Application No. 2020-556041 and is related to U.S. Appl. No. 17/245,895; with English language translation.
Written Opinion issued in PCT/JP2019/043027; dated Dec. 24, 2019.
An Office Action mailed by China National Intellectual Property Administration dated Jan. 1, 2024, which corresponds to Chinese Patent Application No. 201980075340.1 and is related to U.S. Appl. No. 17/245,895; with English language translation.

* cited by examiner

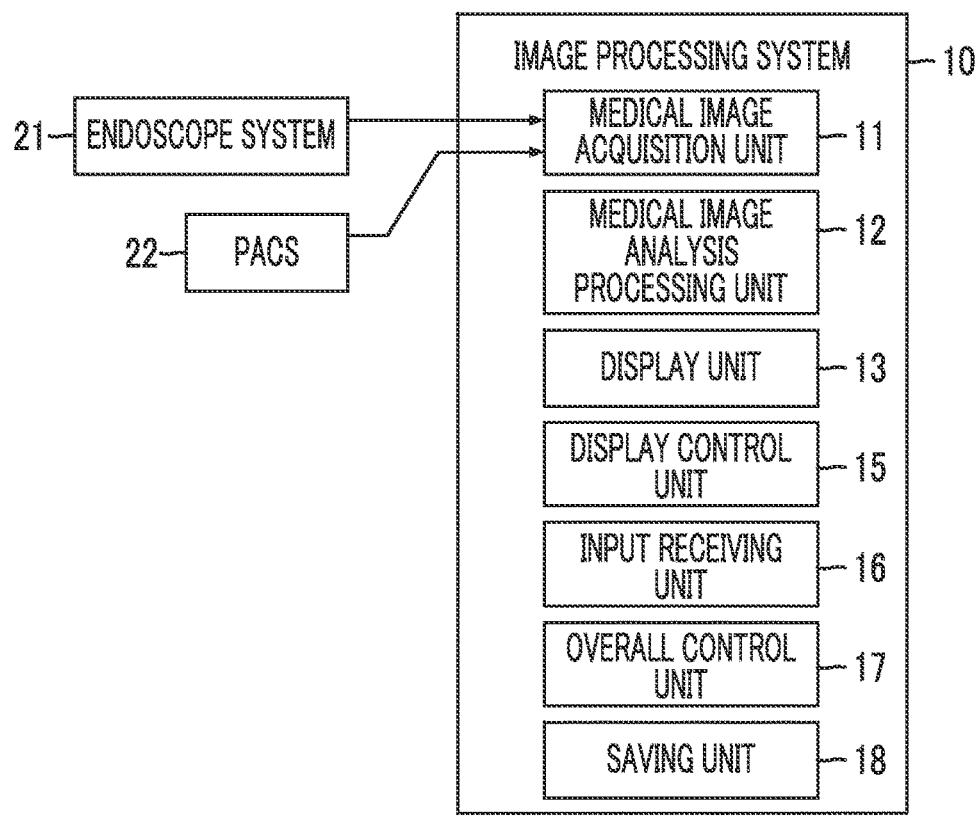
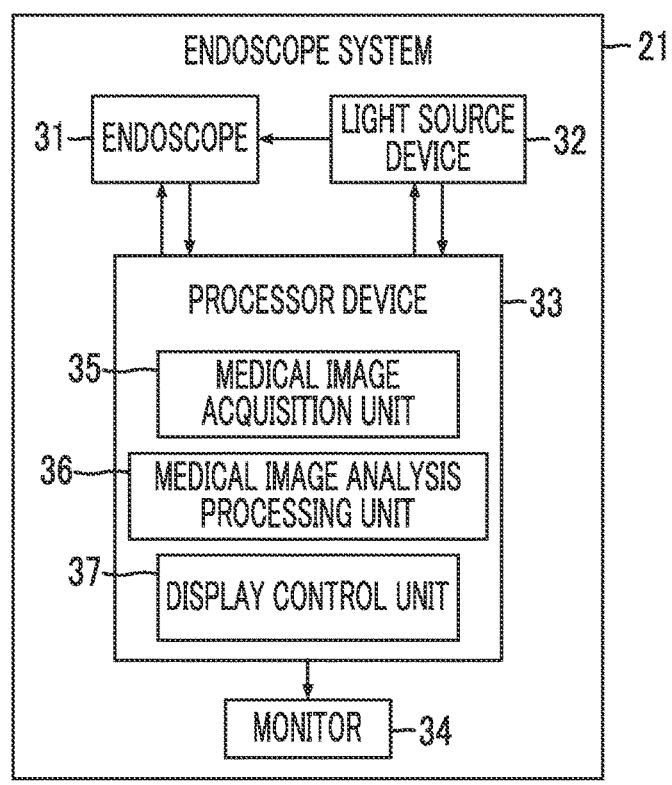

MEDICAL IMAGE PROCESSING SYSTEM

CROSS-REFERENCE TO RELATED APPLICATIONS

This application is a Continuation of PCT International Application No. PCT/JP2019/043027 filed on 1 Nov. 2019, which claims priority under 35 U.S.C § 119(a) to Japanese Patent Application No. 2018-213697 filed on 14 Nov. 2018. The above application is hereby expressly incorporated by reference, in its entirety, into the present application.

BACKGROUND OF THE INVENTION

1. Field of the Invention

The present invention relates to a medical image processing system that determines a disease stage indicating a progress stage of a lesion area based on a medical image.

2. Description of the Related Art

In the current medical field, medical image processing systems that use medical images, such as an endoscope system comprising a light source device, an endoscope, and a processor device, are widespread. Further, in recent years, a technology has been used for calculating a feature amount from a medical image to perform diagnosis on a region included in the medical image, such as a lesion area, based on the calculated feature amount.

For example, in JP2006-334115A (corresponding to US2007/135715A1), in order to detect a medical image having a bleeding site, a feature amount (chromaticity) is calculated for each of regions obtained by dividing the medical image, and it is determined whether or not each region is a bleeding region based on a comparison between the calculated feature amount and a threshold value. Further, in JP2006-166939A, after deleting unnecessary regions from a medical image, a feature amount is calculated for each region of the medical image, and the state of a mucosal region is determined according to the number of regions above a threshold value with respect to the total effective region.

SUMMARY OF THE INVENTION

In diagnosis using medical images, in particular, information on a spatial distribution of feature amounts calculated from medical images is important in a case of specifying a lesion region or determining a disease stage indicating the progress stage of a lesion area or the like with high accuracy. For example, in the early stage of Barrett's esophagus, blood vessels are uniformly distributed throughout, while in the progress stage, there is a tendency for the distribution of blood vessels to vary due to regions where erosions occur and blood vessels cannot be seen and regions where blood vessels are dense. On the other hand, in aforementioned JP2006-334115A and JP2006-166939A, although the region is determined by using the size of the feature amount, there is no description or suggestion about the region determination or the like using the spatial distribution of the feature amount.

An object of the present invention is to provide a medical image processing system capable of determining a disease stage indicating the degree of progress of a lesion area with high accuracy.

According to an aspect of the present invention, there is provided a medical image processing system comprising: a medical image acquisition unit that acquires a medical image obtained by imaging an observation target; a feature amount calculation unit that calculates a feature amount of the observation target for each of pixels of an image region of the medical image or for each of divided regions obtained by dividing the image region of the medical image into a specific size; and a stage determination unit that determines a disease stage of the observation target by using a spatial distribution of the feature amount.

It is preferable that the stage determination unit includes a distribution index value calculation unit that calculates a distribution index value which is an index value of the spatial distribution of the feature amount, and a determination unit that determines the disease stage based on the distribution index value. It is preferable that the distribution index value is a variance of the feature amount, and a degree of progress of the disease stage increases as the variance of the feature amount increases. It is preferable that the distribution index value is an index value related to a spatial distribution of an abnormal region indicating a pixel or a divided region where the feature amount is outside a specific range. It is preferable that the index value related to the spatial distribution of the abnormal region is at least one of the number or an area of the abnormal regions or a ratio occupied by the abnormal region in the image region, and a degree of progress of the disease stage increases as the number or the area of the abnormal regions or the ratio of the abnormal region increases.

It is preferable that the stage determination unit includes a first region integration unit that integrates abnormal regions indicating a pixel or a divided region where the feature amount is outside a specific range, and the distribution index value is an index value related to a spatial distribution of a specific integrated abnormal region that satisfies a specific condition among integrated abnormal regions in which the abnormal regions are integrated by the first region integration unit. It is preferable that the medical image processing system further comprises a second region integration unit that integrates adjacent pixels or divided regions in a case where a feature amount of the adjacent pixels or divided regions is within a feature amount range, and the distribution index value is an index value related to a spatial distribution of an integrated region in which the adjacent pixels or divided regions are integrated by the second region integration unit. It is preferable that the feature amount is at least one of a blood vessel density, a blood vessel contrast, change in a blood vessel width, or an average value of the blood vessel width.

It is preferable that the feature amount calculation unit calculates different types of a plurality of calculation feature amounts for each pixel or for each divided region, and calculates a first calculation value obtained by calculation based on the plurality of calculation feature amounts, as the feature amount. It is preferable that the calculation feature amount is a blood vessel density of a first layer blood vessel and a blood vessel density of a second layer blood vessel different from the first layer blood vessel, and the first calculation value is a ratio of the blood vessel density of the first layer blood vessel to the blood vessel density of the second layer blood vessel.

It is preferable that the feature amount calculation unit calculates different types of a plurality of calculation feature amounts for each pixel or each divided region, and the stage determination unit includes a distribution index value calculation unit that calculates a calculation distribution index value which is an index value of a spatial distribution of each of the calculation feature amounts, and calculates a second calculation value obtained by calculation based on the calculation distribution index value, as a distribution index value, and a determination unit that determines the disease stage based on the distribution index value.

It is preferable that the medical image processing system further comprises an effective region setting unit that sets an effective region in which the disease stage is determinable in the image region, and the feature amount calculation unit calculates the feature amount for each divided region in the effective region. It is preferable that, in a case of calculating the feature amount for each pixel, the feature amount calculation unit calculates a feature amount of a specific region, which is obtained from the specific region including the pixel, as the feature amount for each pixel.

According to the present invention, it is possible to determine a disease stage indicating the degree of progress of a lesion area with high accuracy.

BRIEF DESCRIPTION OF THE DRAWINGS

FIG. 1 is a block diagram showing an image processing system, an endoscope system, and the like.

FIG. 2 is a block diagram showing the endoscope system.

DESCRIPTION OF THE PREFERRED EMBODIMENTS

Figure 3:
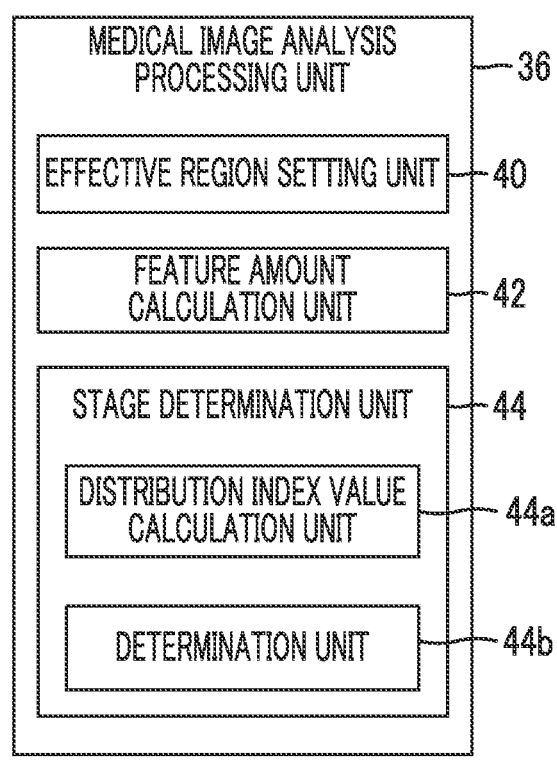
FIG. 3 is a block diagram showing a function of a medical image analysis processing unit.

As shown in FIG. 1, an image processing system 10 comprises a medical image acquisition unit 11, a medical image analysis processing unit 12, a display unit 13, a display control unit 15, an input receiving unit 16, an overall control unit 17, and a saving unit 18. The medical image acquisition unit 11 acquires a medical image including a subject image, directly from an endoscope system 21 or the like that is a medical apparatus, or through a management system such as a picture archiving and communication system (PACS) 22, or other information systems. The medical image is a still image or a motion picture (a so-called examination motion picture). In a case where the medical image is a motion picture, the medical image acquisition unit 11 can acquire a frame image forming a motion picture after examination as a still image. In addition, in a case where the medical image is a motion picture, display of the medical image includes not only displaying a still image of one representative frame forming the motion picture but also reproducing the motion picture once or multiple times. In addition, the medical image acquired by the medical image acquisition unit 11 includes an image automatically captured by a medical apparatus such as the endoscope system 21 regardless of a capturing instruction of a doctor, in addition to an image captured by the doctor using a medical apparatus such as the endoscope system 21. In the present embodiment, since both the image processing system 10 and the endoscope system 21 perform image processing using medical images, both the image processing system 10 and the endoscope system 21 correspond to a medical image processing system. The medical image processing system also includes an ultrasonic diagnostic apparatus that acquires and displays an image in real time.

In the case of being capable of acquiring a plurality of medical images, the medical image acquisition unit 11 can selectively acquire one or a plurality of medical images among these medical images. In addition, the medical image acquisition unit 11 can acquire a plurality of medical images acquired in a plurality of different examinations. For example, it is possible to acquire one or both of a medical image acquired in an examination performed in the past and a medical image acquired in the latest examination. That is, the medical image acquisition unit 11 can acquire a medical image optionally.

In the present embodiment, a plurality of medical images each including a subject image are acquired. More specifically, in a case where a medical image captured in one specific examination is acquired and there are a plurality of medical images captured in one specific examination, a plurality of medical images are acquired out of a series of medical images. In addition, in the present embodiment, the image processing system 10 is connected to the endoscope system 21 to acquire a medical image from the endoscope system 21. That is, in the present embodiment, the medical image is an endoscopic image.

The display unit 13 is a display for displaying a medical image acquired by the medical image acquisition unit 11 and an analysis result of the medical image analysis processing unit 12. A monitor or a display included in a device or the like to which the image processing system 10 is connected can be shared and used as the display unit 13 of the image processing system 10. The display control unit 15 controls a display form of the medical image and the analysis result on the display unit 13.

The input receiving unit 16 receives inputs from a mouse, a keyboard, and other operation devices connected to the image processing system 10. An operation of each unit of the image processing system 10 can be controlled using these operation devices.

The overall control unit 17 controls the overall operation of each unit of the image processing system 10. In a case where the input receiving unit 16 receives an operation input using an operation device, the overall control unit 17 controls each unit of the image processing system 10 according to the operation input.

The saving unit 18 saves a still image or the like of a medical image in a storage device (not shown) such as a memory included in the image processing system 10 or a storage device (not shown) included in a medical apparatus such as the endoscope system 21 or the PACS 22.

As shown in FIG. 2, in the present embodiment, the endoscope system 21 to which the image processing system 10 is connected includes an endoscope 31 that acquires an image by emitting at least one of light in a white wavelength band or light in a specific wavelength band to image the subject, a light source device 32 that emits illumination light to the inside of the subject through the endoscope 31, a processor device 33, and a monitor 34 for displaying a medical image such as an endoscopic image or the like captured using the endoscope 31. The light in a specific wavelength band that is used as illumination light by the endoscope 31 is, for example, light in a shorter wavelength band than the green wavelength band. In particular, the light in a specific wavelength band is light in a blue band or a violet band of the visible range.

The processor device 33 comprises a medical image acquisition unit 35, a medical image analysis processing unit 36, and a display control unit 37. The medical image acquisition unit 35 acquires a medical image output from the endoscope 31. The medical image analysis processing unit 36 performs analysis processing on the medical image acquired by the medical image acquisition unit 35. The processing content of the medical image analysis processing unit 36 is the same as the processing content of the medical image analysis processing unit 12 of the image processing system 10. The display control unit 37 displays the medical image obtained by the medical image analysis processing unit 36 on the monitor 34 (display unit). The processor device 33 is connected to the image processing system 10. The medical image acquisition unit 35 is the same as the medical image acquisition unit 11, the medical image analysis processing unit 36 is the same as the medical image analysis processing unit 12, and the display control unit 37 is the same as the display control unit 15.

The medical image analysis processing unit 36 performs analysis processing using the medical image acquired by the medical image acquisition unit 11. As shown in FIG. 3, the medical image analysis processing unit 36 comprises an effective region setting unit 40, a feature amount calculation unit 42, and a stage determination unit 44.

Figure 4:
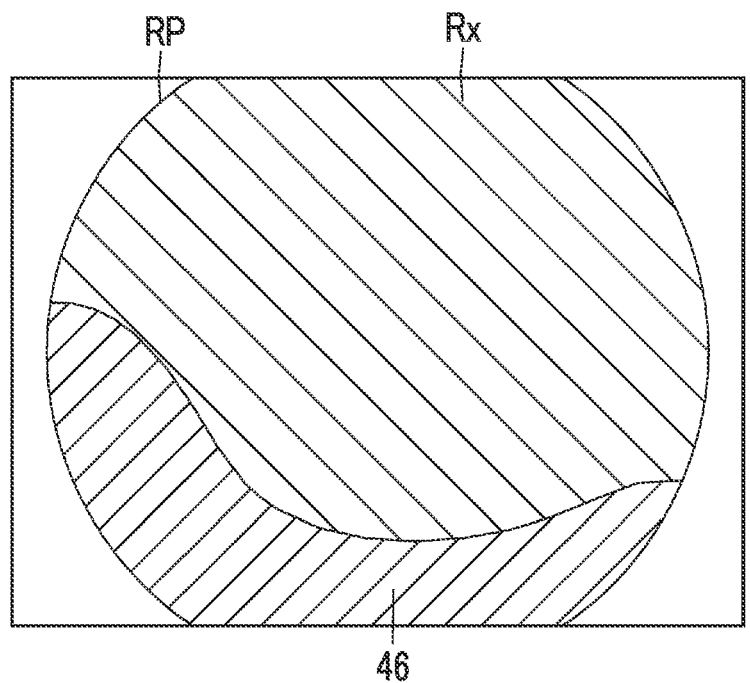
FIG. 4 is an image diagram of a medical image showing an image region and an effective region.

The effective region setting unit 40 sets an effective region in the image region of the medical image in which the stage determination unit 44 can determine the disease stage. Therefore, from the image region of the medical image, an indeterminable region in which the disease stage cannot be determined or which interferes with determination of the stage is removed. For example, as shown in FIG. 4, in an image region RP, a dark area 46 having a low pixel value is set as an indeterminable region, and the dark area 46 is removed from the image region RP. The image region RP is a display region that displays the entire image of the observation target imaged by the endoscope 31. Then, the region in which the dark area 46 is removed from the image region RP is set as an effective region Rx.

In addition to the dark area 46, it is preferable that specific pools such as puddles, blood pools, and the like that cover an observation target, distortion generated around the image region RP (distortion due to an objective lens used to image an observation target), image blur, bubbles containing air, and the like are set as indeterminable regions. For example, since a specific pool has a specific color, it is possible to remove the specific pool by a process of removing the specific color. Further, since the bubbles have a circular shape, it is possible to remove the bubbles by removing the circular structure.

Figure 5:
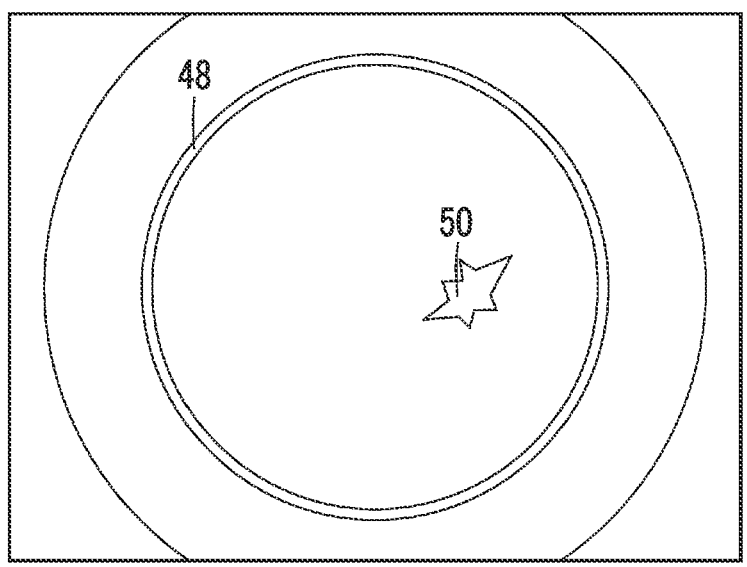
FIG. 5 is an image diagram of a medical image showing an edge of a cap and a specular reflection.

Further, in a case where a cap is attached to the distal end of the insertion part of the endoscope 31 and an edge 48 of the cap is reflected in the image region of the medical image as shown in FIG. 5, the image of the edge 48 of the cap is also set as an indeterminable region because it interferes with the determination of the disease stage by the stage determination unit 44. Further, a specular reflection 50 caused by the observation target being covered with a transparent mucous membrane is also set as an indeterminable region because it interferes with the determination of the disease stage by the stage determination unit 44. Then, the effective region setting unit 40 sets the region in which the edge 48 of the cap or the specular reflection 50 is removed from the image region RP as the effective region. An image showing an indeterminable region may be created, the image of the indeterminable region may be learned by a learning unit (not shown) of the processor device 33, and the acquired medical image may be input to the learning unit to specify the indeterminable region.

Figure 6:
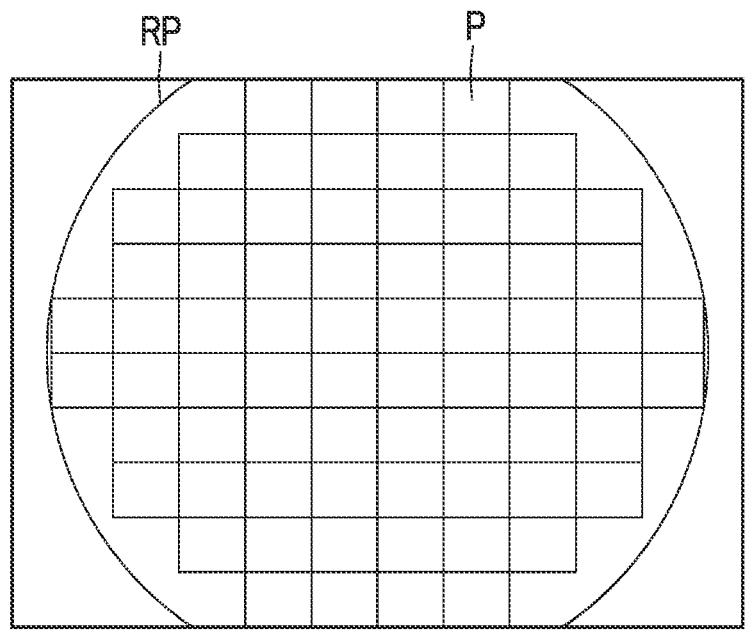
FIG. 6 is an image diagram of a medical image showing an image region and a divided region.
Figure 7A:
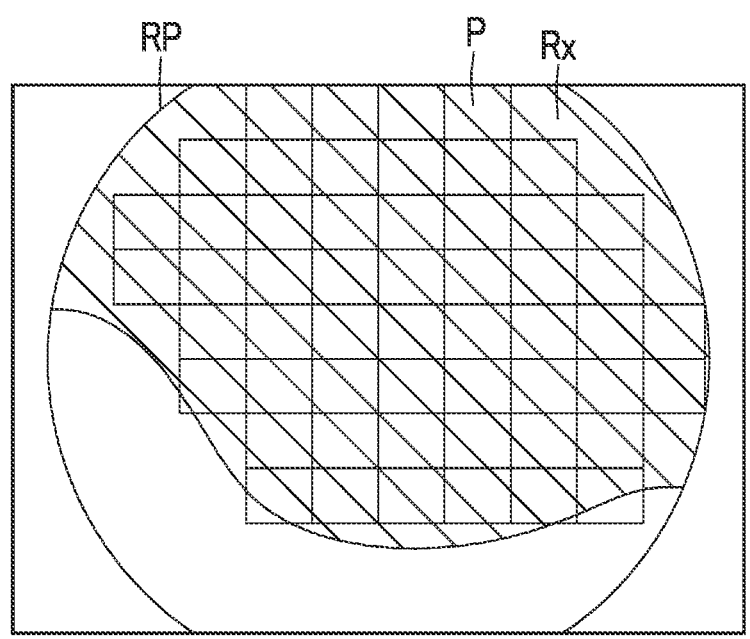
FIG. 7A is an image diagram of a medical image showing an image region and a divided region within an effective region.
Figure 7B:
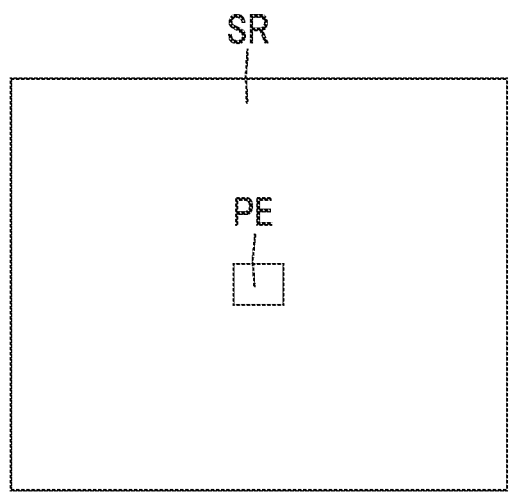
FIG. 7B is an explanatory diagram showing a pixel PE and a specific region SR.

As shown in FIG. 6, the feature amount calculation unit 42 calculates a feature amount of the observation target for each divided region P obtained by dividing the image region RP of the medical image into a specific size. For example, in a case where the image size of a medical image is 640×480, and 16 divisions are made vertically and horizontally, the specific size of the divided region is about 40×30 (the specific size of the left and right peripheral parts is smaller than that of other parts). Since the feature amount is used for determining the disease stage, as shown in FIG. 7A, it is preferable that the feature amount calculation unit 42 calculates the feature amount of the observation target for the divided region P in the effective region Rx where the disease stage can be determined. In addition, instead of calculating the feature amount for each divided region P, the feature amount calculation unit 42 may calculate the feature amount for each pixel of the image region RP. In this case, for example, as shown in FIG. 7B, it is preferable to set a specific region SR of about 40×30 centered on a pixel PE of interest, and calculate the feature amount obtained in the specific region SR as the feature amount of the pixel of interest.

It is preferable that the feature amount calculation unit 42 calculates, for example, a blood vessel density of blood vessels, the contrast of a blood vessel, change in blood vessel width, an average value of blood vessel widths, and the like included in the specific region SR or each divided region P as a feature amount.

The blood vessel density is a proportion of blood vessels included in the specific region SR or the divided region P. The density of blood vessels is a proportion occupied by the blood vessels in all the pixels of the divided region P. For blood vessels, it is preferable to use a pixel region having a pixel value lower than that of the surroundings as a blood vessel.

The contrast of a blood vessel is a relative contrast of the blood vessel with respect to the mucous membrane of an observation target. The contrast of a blood vessel is calculated by, for example, "YV/YM" or "(YV−YM)/(YV+YM)" using the brightness YV of the blood vessel and the brightness YM of the mucous membrane.

The change in blood vessel width is a blood vessel index value related to a variation in blood vessel width (distance between boundary lines between the blood vessel and the mucous membrane) of blood vessels included in the specific region SR or the divided region P, and is also referred to as a degree of caliber disparity. The change in blood vessel width is, for example, the rate of change in blood vessel width (also referred to as the degree of expansion). The rate of change in blood vessel diameter is obtained by "rate of change in blood vessel diameter (%)=minimum diameter/maximum diameter×100" using the thickness of the thinnest part of the blood vessel (minimum diameter) and the thickness of the thickest part of the blood vessel (maximum diameter). The blood vessel width is obtained by counting, for example, the number of pixels in the lateral direction of a blood vessel in the orthogonal direction at specific intervals along the central axis of the extracted blood vessel.

The average value of blood vessel widths is an average value of blood vessel widths of blood vessels included in the specific region SR or the divided region P. Specifically, the average value of blood vessel widths is calculated by dividing the total blood vessel width of blood vessels in the divided region P by the number of blood vessels in the divided region P.

In addition to the above, the feature amounts calculated by the feature amount calculation unit 42 include the complexity of blood vessel width change, the number of blood vessels, the number of crossings between blood vessels, the length of a blood vessel, the interval between blood vessels, the depth of a blood vessel, the height difference of blood vessels, the inclination of a blood vessel, the area of a blood vessel, the color of a blood vessel, the degree of meandering of a blood vessel, the blood concentration of a blood vessel, the oxygen saturation of a blood vessel, the traveling pattern of a blood vessel, and the blood flow rate of a blood vessel.

The complexity of blood vessel width change (hereinafter referred to as "complexity of width change") is a blood vessel index value indicating how complicated a change is in a case where the blood vessel width of the blood vessel included in the specific region SR or the divided region P is changed, and a blood vessel index value calculated by combining a plurality of blood vessel index values (that is, a rate of change in blood vessel diameter, a proportion of a small diameter portion, or a proportion of a large diameter portion) indicating the change in blood vessel width. The complexity of the thickness change can be obtained, for example, by the product of the rate of change in the blood vessel diameter and the proportion of the small diameter portion.

The number of blood vessels is the number of blood vessels extracted in the specific region SR or the divided region P. The number of blood vessels is calculated using, for example, the number of branch points (number of branches) of the extracted blood vessels, the number of intersections with other blood vessels (number of crossings), and the like. The branch angle of a blood vessel is an angle formed by two blood vessels at a branch point. The distance between branch points is a linear distance between any branch point and a branch point adjacent thereto, or a length along a blood vessel from any branch point to a branch point adjacent thereto.

The number of crossings between blood vessels is the number of intersections at which blood vessels having different submucosal depths cross each other in the specific region SR or the divided region P. More specifically, the number of crossings between blood vessels is the number of blood vessels, which are located at relatively shallow submucosal positions, crossing blood vessels located at deep positions.

The length of a blood vessel is the number of pixels counted in the longitudinal direction of the blood vessel extracted from the specific region SR or the divided region P.

The interval between blood vessels is the number of pixels showing the mucous membrane between edges of the blood vessels extracted from the specific region SR or the divided region P. In a case where the number of extracted blood vessels is one, the interval between blood vessels has no value.

The depth of a blood vessel is measured with respect to the mucous membrane (more specifically, the surface of the mucous membrane). The depth of a blood vessel with respect to the mucous membrane can be calculated, for example, based on the color of the blood vessel. In the case of the special observation image, for example, a superficial blood vessel near the mucosal surface (shallow submucosal position) is expressed by a magenta type color, and a middle-deep blood vessel far from the mucosal surface (deep submucosal position) is expressed by a cyan type color. Therefore, the depth of the blood vessel with respect to the mucous membrane is calculated for each pixel based on the balance of the signals of respective colors of R, G, and B of the pixels extracted as a blood vessel.

The height difference of a blood vessel is the magnitude of the difference in the depth of the blood vessel included in the specific region SR or the divided region P. For example, the height difference of one blood vessel of interest is obtained by the difference between the depth of the deepest part (maximum depth) of the blood vessel and the depth of the shallowest part (minimum depth) thereof. In a case where the depth is constant, the height difference is zero.

The inclination of a blood vessel is the rate of change in the depth of the blood vessel included in the specific region SR or the divided region P, and is calculated using the length of the blood vessel and the depth of the blood vessel. That is, the inclination of a blood vessel is obtained by "inclination of blood vessels=depth of blood vessel/length of blood vessel". The blood vessel may be divided into a plurality of sections, and the inclination of the blood vessel may be calculated in each section.

The area of a blood vessel is the number of pixels of the blood vessel pixels included in the specific region SR or the divided region P, or a value proportional to the number of pixels of the pixels extracted as a blood vessel. The area of a blood vessel is calculated within the region of interest, outside the region of interest, or for the entire endoscopic image.

The color of a blood vessel is each value of RGB of pixels showing the blood vessels included in the specific region SR or the divided region P. The change in the color of a blood vessel is a difference or ratio between the maximum value and the minimum value of each value of the RGB of the pixels showing the blood vessels. For example, the ratio between the maximum value and the minimum value of the B value of a pixel showing the blood vessel, the ratio between the maximum value and the minimum value of the G value thereof, or the ratio between the maximum value and the minimum value of the R value thereof indicates a change in the color of the blood vessel. Needless to say, conversion into complementary colors may be performed to calculate the color of the blood vessel and a change in the color of the blood vessel for each value of cyan, magenta, yellow, green, and the like.

The degree of meandering of a blood vessel is a blood vessel index value indicating the width of a range in which the blood vessel included in the specific region SR or the divided region P travels meandering. The degree of meandering of blood vessels is, for example, the area (number of pixels) of the smallest rectangle including the blood vessel for which the degree of meandering is to be calculated. Further, the ratio of the length of the blood vessel to the linear distance between the start point and the end point of the blood vessel may be used as the degree of meandering of the blood vessel.

The blood concentration of a blood vessel is a blood vessel index value proportional to the amount of hemoglobin in a blood vessel included in the specific region SR or the divided region P. Since the ratio (G/R) of the G value to the R value of a pixel showing a blood vessel is proportional to the amount of hemoglobin, the blood concentration can be calculated for each pixel by calculating the G/R value.

The oxygen saturation of a blood vessel is the amount of oxygenated hemoglobin to the total amount of hemoglobin (total amount of oxygenated hemoglobin and reduced hemoglobin) in a blood vessel included in the specific region SR or the divided region P. The oxygen saturation can be calculated using an endoscopic image obtained in a case where the observation target is illuminated with light in a specific wavelength band (for example, blue light with a wavelength of about 470±10 nm) having a large difference between the light absorption coefficients of oxygenated hemoglobin and reduced hemoglobin. In a case where blue light with a wavelength of about 470±10 nm is used, the B value of the pixel showing the blood vessel correlates with the oxygen saturation. Therefore, by using a table or the like that associates the B value with the oxygen saturation, it is possible to calculate the oxygen saturation of each pixel showing the blood vessel.

The proportion of arteries is the proportion of the number of pixels of arteries to the number of pixels of all blood vessels. Similarly, the proportion of veins is the proportion of the number of pixels of veins to the number of pixels of all blood vessels. Arteries and veins can be distinguished by oxygen saturation. For example, assuming that a blood vessel having an oxygen saturation of 70% or more is an artery and a blood vessel having an oxygen saturation of less than 70% is a vein, extracted blood vessels can be distinguished into arteries and veins. Therefore, it is possible to calculate the proportion of arteries and the proportion of veins.

The concentration of an administered coloring agent is the concentration of a coloring agent sprayed on the observation target or the concentration of a coloring agent injected into the blood vessel by intravenous injection. The concentration of the administered coloring agent is calculated, for example, by the ratio of the pixel value of the coloring agent color to the pixel value of a pixel other than the coloring agent color. For example, in a case where a coloring agent for coloring in blue is administered, B/G, B/R, and the like indicate the concentration of the coloring agent fixed (or temporarily adhered) to the observation target. B/G is the ratio of the pixel value of the blue image of the medical image to the pixel value of the green image of the medical image, and B/R is the ratio of the pixel value of the blue image of the medical image to the pixel value of the red image of the medical image.

The traveling pattern of a blood vessel is a blood vessel index value related to the traveling direction of a blood vessel included in the specific region SR or the divided region P. The traveling pattern of a blood vessels is, for example, an average angle (traveling direction) of a blood vessel with respect to an optionally set reference line, a variance (variation in the traveling direction) of an angle formed by a blood vessel with respect to an optionally set reference line, and the like.

The blood flow rate of a blood vessel is the number of red blood cells passing through in a blood vessel included in the specific region SR or the divided region P per unit time. The blood flow rate of a blood vessel can be obtained by calculating the Doppler shift frequency of each pixel showing a blood vessel in the endoscopic image using a signal obtained by an ultrasonic probe, for example, in a case where the ultrasonic probe is used together through a forceps channel of the endoscope 31 or the like.

The stage determination unit 44 determines the disease stage of the observation target by using the spatial distribution of the feature amount calculated by the feature amount calculation unit 42. The stage determination unit 44 comprises a distribution index value calculation unit 44a that calculates a distribution index value which is an index value of the spatial distribution of the feature amount, and a determination unit 44b that determines the disease stage based on the distribution index value (refer to FIG. 3). The spatial distribution of the feature amount means the spread of the feature amount in the image region RP, and specifically, indicates the difference in the size of the feature amount between pixels in the image region.

Here, the disease stage is preferably represented by the degree of progress of the lesion area. In general, it is considered that the degree of progress of the disease stage increases as the spatial distribution of the feature amount varies. For example, in a case where the lesion area is Barrett's esophagus, in the early stage, "the blood vessels are uniformly distributed throughout" and "the blood vessel width does not change much". That is, in the case of the early stage, it is considered that the spatial distribution of the feature amount has a little variation. On the other hand, in the progress stage, "there is a region where the blood vessel cannot be seen due to inflammation and erosion", "the blood vessel width changes depending on the region", and "the change in blood vessel width becomes large". That is, in the case of the progress stage, it is considered that the spatial distribution of the feature amount varies.

In the present embodiment, the distribution index value is used to determine the disease stage, but the disease stage may be determined by other methods. For example, a learning unit (not shown) of the processor device 33 is made to learn a spatial distribution image of the feature amount and the disease stage determined from the distribution image as learning data. Machine learning methods such as deep learning are used for learning. Then, by inputting the spatial distribution image of the feature amount calculated by the feature amount calculation unit 42 into the learning unit, the disease stage is output from the learning unit.

Figure 8:
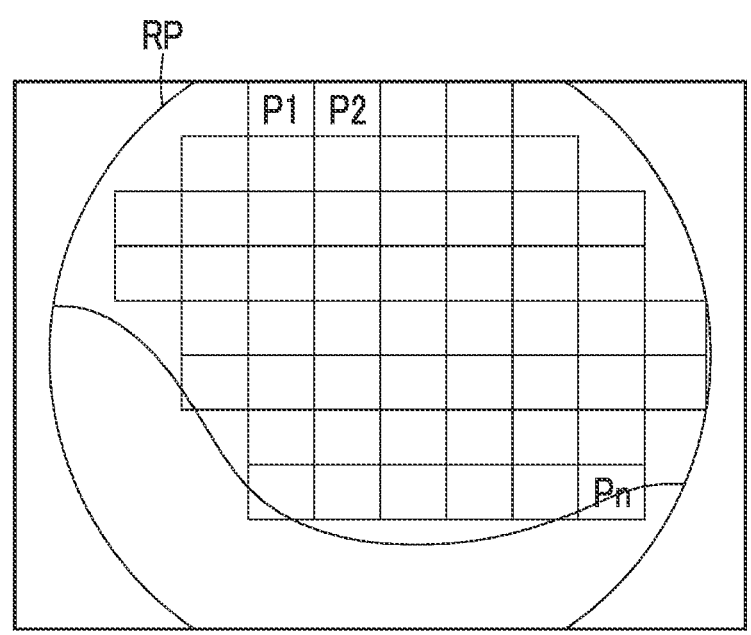
FIG. 8 is an image diagram of a medical image showing divided regions P1, P2, . . . , and Pn.

The distribution index value calculation unit 44a obtains, for example, the variance of the feature amount as the distribution index value. Specifically, in a case where the feature amount is calculated for each divided region, as shown in FIG. 8, a total value S is calculated by adding all the feature amounts of divided regions P1, P2, . . . , and Pn, and an average feature amount Ave is calculated by dividing the total value S by the number N of the divided regions. Next, a squared deviation V1 (=(feature amount of divided region P1−Ave)$^2$) is calculated by squaring the feature amount of the divided region P1 minus the average feature amount Ave. Similarly, for the feature amounts of the divided regions P2 to Pn, squared deviations V2 (=(feature amount of divided region P2–Ave)$^2$), ..., and Vn (=(feature amount of divided region Pn–Ave)$^2$) are calculated by squaring each of the feature amounts minus the average feature amount Ave. Then, a variance Vx is obtained by summing all the calculated squared deviations V1, V2, ..., and Vn.

In a case where the feature amount is calculated for each pixel, the total value is calculated by adding all the feature amounts calculated for each pixel, and the average feature amount is calculated by dividing the total value by the number of pixels in the effective region. Next, the squared deviation (=(feature amount of each pixel–average feature amount)$^2$) is calculated by squaring the feature amount of each pixel minus the average feature amount. Then, the variance is obtained by summing all the squared deviations in the effective region.

The determination unit 44b determines the disease stage based on the variance obtained by the distribution index value calculation unit 44a. In this case, it is considered that the spatial distribution of the feature amount varies as the variance of the feature amount increases, so that it is determined that the degree of progress of the disease stage increases.

Figure 9:
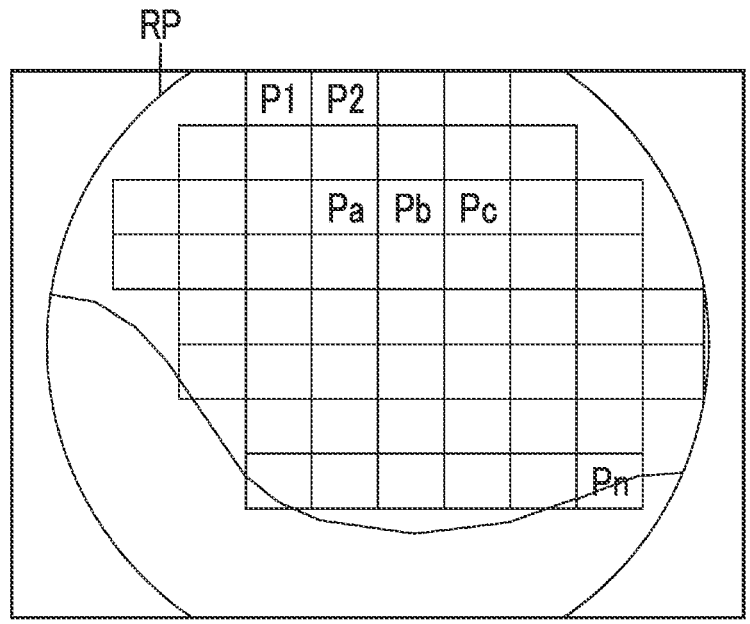
FIG. 9 is an image diagram of a medical image showing divided regions Pa, Pb, and Pc which are abnormal regions.

The distribution index value calculation unit 44a specifies, for example, a pixel or a divided region where the feature amount is outside a specific range as an abnormal region, and calculates an index value related to a spatial distribution of the abnormal region as a distribution index value. In the case of the divided region, for example, as shown in FIG. 9, as for the abnormal region, among the divided regions P1, P2, ..., Pa, Pb, Pc, ..., and Pn, the divided regions Pa, Pb, and Pc where the feature amount is outside the specific range are specified as abnormal regions. As an index value related to the spatial distribution of the abnormal region, there is the number and area of the abnormal regions, or the ratio of the area occupied by the abnormal region in the image region RP (area ratio of the abnormal region). For example, in a case where the abnormal region is divided regions Pa, Pb, and Pc, the area of each divided region is M, and the number of divided regions is N, the number of abnormal regions is "3", the area of the abnormal regions is "3M", and the area ratio of the abnormal regions is "3M/NM". The spatial distribution of the abnormal region means the spread of the abnormal region in the image region RP, and specifically, indicates the difference between the abnormal regions of the image region RP. Further, the "spatial distribution of a specific integrated abnormal region" or the "spatial distribution of an integrated region" shown below is also defined in the same manner.

The determination unit 44b determines the disease stage based on the index value related to the spatial distribution of the abnormal region. For example, as an index value related to the spatial distribution of the abnormal region, it is considered that the spatial distribution of the feature amount varies as the number or an area of the abnormal regions or the area ratio of the abnormal regions increases. Therefore, it is determined that the degree of progress of the disease stage increases. In either case of calculating the feature amount for each pixel or calculating the feature amount for each divided region, it is possible to determine the degree of progress of the disease stage based on the number of pixels in the abnormal region where the feature amount is outside the specific range.

Second Embodiment

In a second embodiment, abnormal regions indicating a pixels or a divided region where a feature amount is outside a specific range are integrated, and an index value related to the spatial distribution of a specific integrated abnormal region that satisfies a specific condition among integrated abnormal regions in which the abnormal regions are integrated is calculated as a distribution index value. In the second embodiment, the index value related to the spatial distribution of the specific integrated abnormal region is, for example, at least one of the number or the area of the specific integrated abnormal regions, or the ratio occupied by the integrated abnormal region in the image region.

Figure 10:
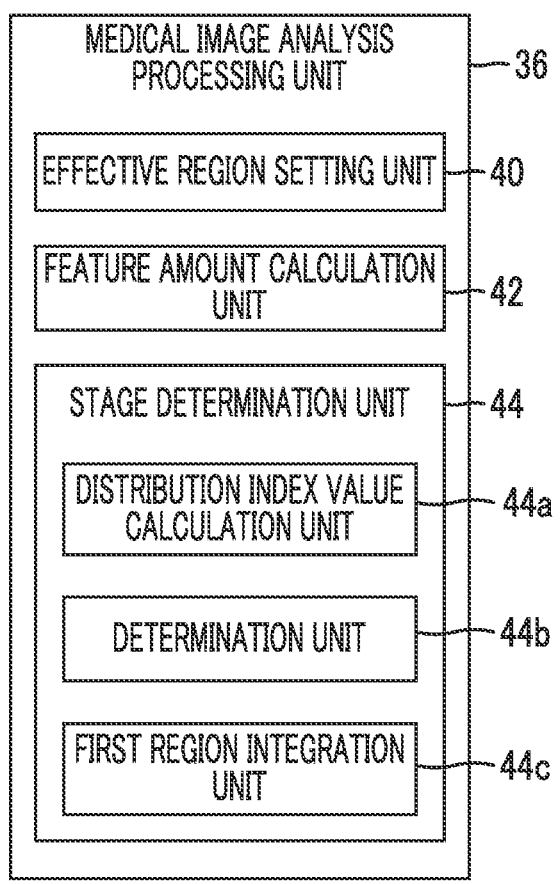
FIG. 10 is a block diagram showing a medical image analysis processing unit including a first region integration unit.

Also in the second embodiment, the distribution index value calculation unit 44a specifies an abnormal region indicating a pixel or a divided region where the feature amount is outside the specific range. Here, the index value related to the spatial distribution of the abnormal region is not used as the distribution index value as it is. Then, as shown in FIG. 10, a first region integration unit 44c provided in the medical image analysis processing unit 36 integrates a plurality of adjacent abnormal regions as integrated abnormal regions in a case where the abnormal regions are adjacent to each other. Then, the first region integration unit 44c sets an integrated abnormal region having an area of a certain value or more or an integrated abnormal region occupying a certain ratio or more in the image region as a specific integrated abnormal region satisfying a specific condition. Then, the distribution index value calculation unit 44a calculates at least one of the number or the area of the specific integrated abnormal regions or the ratio occupied by the specific integrated abnormal region in the image region as the distribution index value.

Figure 11:
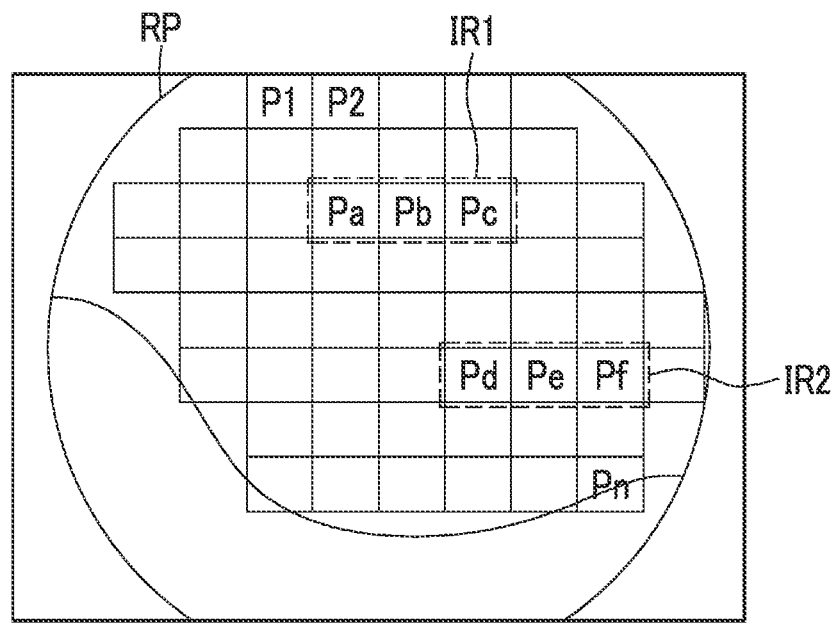
FIG. 11 is an image diagram of a medical image showing integrated abnormal regions IR1 and IR2.

Taking the case where the abnormal region is a divided region as an example, for example, as shown in FIG. 11, in a case where the abnormal regions Pa, Pb, and Pc are adjacent to each other, and abnormal regions Pd, Pe, and Pf are distributed adjacent to each other at positions away from these abnormal regions Pa, Pb, and Pc, the first region integration unit 44c integrates the abnormal regions Pa, Pb, and Pc into an integrated abnormal region IR1, and integrates the abnormal regions Pd, Pe, and Pf into an integrated abnormal region IR2. Here, assuming that the areas of the integrated abnormal regions IR1 and IR2 are below a certain value, the integrated abnormal regions IR1 and IR2 are not set as specific integrated abnormal regions.

Figure 12:
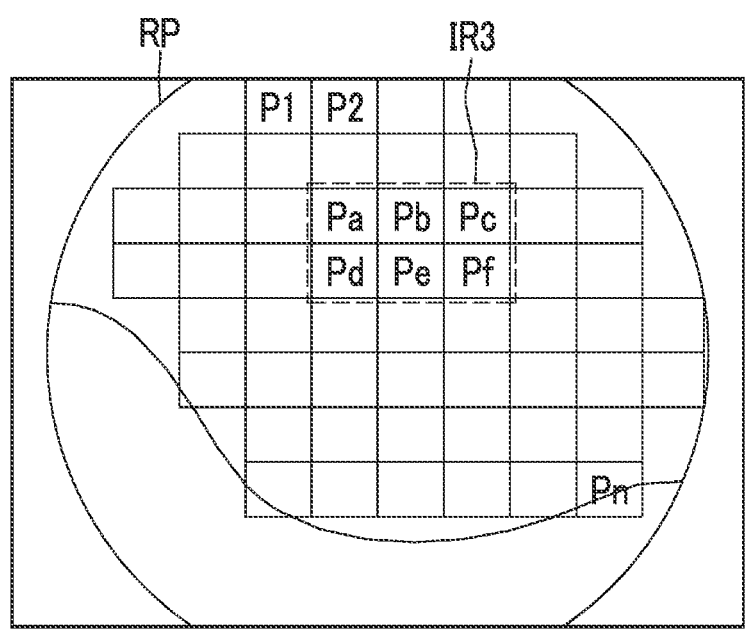
FIG. 12 is an image diagram of a medical image showing an integrated abnormal region IR3.

On the other hand, as shown in FIG. 12, in a case where the abnormal regions Pa, Pb, Pc, Pd, Pe, and Pf are distributed adjacent to each other, the first region integration unit 44c integrates the abnormal regions Pa, Pb, Pc, Pd, Pe, and Pf into an integrated abnormal region IR3. Then, assuming that the area of the integrated abnormal region IR3 is equal to or larger than a certain value, the integrated abnormal region IR3 is set as a specific integrated abnormal region. At least one of the number or the area of the integrated abnormal regions IR3 or the ratio occupied by the specific integrated abnormal region IR3 in the image region RP is calculated as the distribution index value.

In a case where the number or the area of the specific integrated abnormal regions or the ratio occupied by the specific integrated abnormal region in the image region is calculated as the distribution index value, the determination unit 44b determines the disease stage based on the area of the specific integrated abnormal regions and the like. For example, it is considered that the spatial distribution of the feature amount varies as the area of the specific integrated abnormal region increases, so that it is determined that the degree of progress of the disease stage increases. In either case of calculating the feature amount for each pixel or calculating the feature amount for each divided region, it is possible to determine the degree of progress of the disease stage based on the number of specific integrated abnormal regions and the like.

Figure 13:
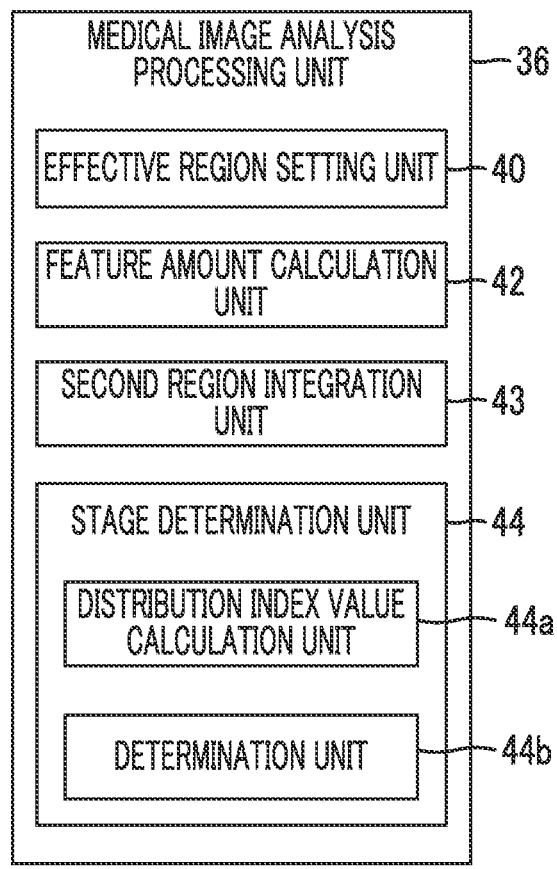
FIG. 13 is a block diagram showing a medical image analysis processing unit including a second region integration unit.

In the second embodiment, instead of integrating the abnormal regions, in a case where a feature amount of adjacent pixels or divided regions is within a feature amount range, the adjacent pixels or divided regions may be integrated. The integration of the pixels or the divided regions is performed by a second region integration unit 43 in the medical image analysis processing unit 36 shown in FIG. 13. Then, the distribution index value calculation unit 44*a* calculates an index value related to the spatial distribution of the integrated region in which the adjacent pixels or divided regions are integrated, as the distribution index value. The index value related to the spatial distribution of the integrated region is, for example, the variance of the integrated region.

Figure 14:
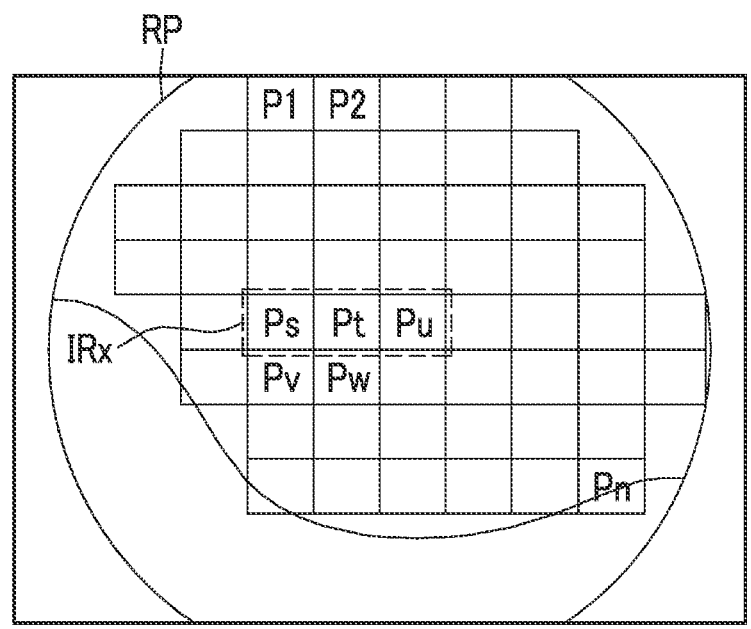
FIG. 14 is an image diagram of a medical image showing an integrated abnormal region IRx.

Taking the case of the divided region as an example, for example, as shown in FIG. 14, in a case where a divided region Ps having the feature amount Cs, a divided region Pt having a feature amount Ct, a divided region Pu having a feature amount Cu, a divided region Pv having a feature amount Cv, and a divided region Pw having a feature amount Cw are distributed adjacent to each other, the feature amounts Cs, Ct, and Cu are within a feature amount range, and in a case where the feature amounts Cv and Cw are outside the feature amount range, the divided regions Ps, Pt, and Pu are integrated to form an integrated region IRx. Then, the variance of the integrated region IRx is calculated as a distribution index value.

In a case where the number or the area of the integrated regions or the ratio occupied by the integrated region in the image region is calculated as the distribution index value, the determination unit 44*b* determines the disease stage based on the number of the integrated regions and the like. For example, it is considered that the spatial distribution of the feature amount varies as the number of the integrated regions increases, so that it is determined that the degree of progress of the disease stage increases. In either case of calculating the feature amount for each pixel or calculating the feature amount for each divided region, it is possible to determine the degree of progress of the disease stage based on the number of integrated regions and the like.

In the first and second embodiments, as the feature amount, the blood vessel density, the blood vessel contrast, the change in blood vessel width, the average value of the blood vessel width, and the like are calculated, but a combination thereof may be calculated as the feature amount. For example, the feature amount calculation unit 42 may calculate different types of a plurality of calculation feature amounts for each pixel or for each divided region to calculate a first calculation value obtained by calculation based on the plurality of calculation feature amounts, as the feature amount. In a case of calculating a plurality of calculation feature amounts for each pixel, the plurality of calculation feature amounts calculated in the specific region SR is preferably used as the feature amount for each pixel, as in the above embodiment.

For example, in a case where two calculation feature amounts of a blood vessel density of a most superficial blood vessel (first layer blood vessel) and a blood vessel density of a superficial blood vessel (second layer blood vessel) located in a region deeper than the most superficial blood vessel are calculated in the specific region SR or each divided region, a blood vessel density ratio (first calculation value) obtained by dividing the blood vessel density of the most superficial blood vessel by the blood vessel density of the superficial blood vessel may be calculated as the feature amount. In this case, for a blood vessel density of the most superficial blood vessel, it is preferable to calculate a blood vessel density of the most superficial blood vessel included in each divided region by using a 410 nm-medical image obtained based on illumination light including narrow-band light of 410 nm. In addition, for a blood vessel density of the superficial blood vessel, it is preferable to calculate a blood vessel density of the superficial blood vessel included in each divided region by using a 450 nm-medical image obtained based on illumination light including narrow-band light of 450 nm.

Further, the feature amount calculation unit 42 calculates different types of a plurality of calculation feature amounts for each specific region SR or for each divided region, and then the distribution index value calculation unit 44*a* may calculate a calculation distribution index value which is an index value of a spatial distribution of each of the calculation feature amounts, and calculate a second calculation value obtained by calculation based on the calculated calculation distribution index value, as a distribution index value.

Further, as described above, in the case where two calculation feature amounts of a blood vessel density of a most superficial blood vessel and a blood vessel density of a superficial blood vessel located in a region deeper than the most superficial blood vessel are calculated in the specific region SR or each divided region, a distribution index value of the most superficial blood vessel, which is an index value of the spatial distribution of the blood vessel density of the most superficial blood vessel, is calculated, and a distribution index value of the superficial blood vessel, which is an index value of the spatial distribution of the blood vessel density of the superficial blood vessel, is calculated. Then, a distribution index value ratio (second calculation value) obtained by dividing the distribution index value of the most superficial blood vessel by the distribution index value of the superficial blood vessel may be calculated as the distribution index value.

In addition, the image processing system 10, the endoscope system 21, and various devices or systems including the image processing system 10 can be used with the following various modifications.

As the medical image, it is possible to use a normal light image obtained by emitting light in a white band or light in a plurality of wavelength bands as light in the white band.

In a case where an image obtained by emitting light in a specific wavelength band is used as the medical image, a band narrower than the white wavelength band can be used as the specific wavelength band.

The specific wavelength band is, for example, a blue band or a green band of a visible range.

In a case where the specific wavelength band is the blue band or the green band of a visible range, it is preferable that the specific wavelength band includes a wavelength band of 390 nm to 450 nm or a wavelength band of 530 nm to 550 nm and that light in the specific wavelength band has a peak wavelength within the wavelength band of 390 nm to 450 nm or the wavelength band of 530 nm to 550 nm.

The specific wavelength band is, for example, a red band of a visible range.

In a case where the specific wavelength band is the red band of a visible range, it is preferable that the specific wavelength band includes a wavelength band of 585 nm to 615 nm or a wavelength band of 610 nm to 730 nm and that light in the specific wavelength band has a peak wavelength within the wavelength band of 585 nm to 615 nm or the wavelength band of 610 nm to 730 nm.

The specific wavelength band can include, for example, a wavelength band in which light absorption coefficients of oxygenated hemoglobin and reduced hemoglobin are different, and light in the specific wavelength band can have a peak wavelength in the wavelength band in which light absorption coefficients of oxygenated hemoglobin and reduced hemoglobin are different.

In a case where the specific wavelength band includes a wavelength band in which the light absorption coefficients of oxygenated hemoglobin and reduced hemoglobin are different and light in the specific wavelength band has a peak wavelength in the wavelength band in which the light absorption coefficients of oxygenated hemoglobin and reduced hemoglobin are different, it is preferable that the specific wavelength band includes a wavelength band of 400±10 nm, 440±10 nm, 470±10 nm, or 600 nm to 750 nm and that light in the specific wavelength band has a peak wavelength within the wavelength band of 400±10 nm, 440±10 nm, 470±10 nm, or 600 nm to 750 nm.

In a case where the medical image is an in-vivo image of the living body, the in-vivo image can have information on fluorescence emitted from the fluorescent material in the living body.

In addition, as the fluorescence, fluorescence obtained by emitting excitation light having a peak wavelength of 390 nm to 470 nm to the inside of the living body can be used.

In a case where the medical image is an in-vivo image of the living body, the wavelength band of infrared light can be used as the specific wavelength band described above.

In a case where the medical image is an in-vivo image of the living body and the wavelength band of infrared light is used as the specific wavelength band described above, it is preferable that the specific wavelength band includes a wavelength band of 790 nm to 820 nm or 905 nm to 970 nm and that light in the specific wavelength band has a peak wavelength within the wavelength band of 790 nm to 820 nm or 905 nm to 970 nm.

The medical image acquisition unit 11 can have a special light image acquisition unit that acquires a special light image having a signal in a specific wavelength band on the basis of a normal light image obtained by emitting light in a white band or light in a plurality of wavelength bands as light in the white band. In this case, the special light image can be used as the medical image.

The signal in a specific wavelength band can be obtained by calculation based on the color information of RGB or CMY included in the normal light image.

It is possible to comprise a feature amount image generation unit that generates a feature amount image by calculation based on at least one of the normal light image obtained by emitting light in a white band or light in a plurality of wavelength bands as light in the white band or the special light image obtained by emitting light in a specific wavelength band. In this case, the feature amount image can be used as the medical image.

In the endoscope system 21, a capsule endoscope can be used as the endoscope 31. In this case, the light source device 32 and a part of the processor device 33 can be mounted in the capsule endoscope.

In the embodiment, the present invention is applied to the endoscope system that performs processing on the endoscopic image as one of the medical images. However, the present invention can also be applied to a medical image processing system that processes medical images other than the endoscopic image. The present invention can also be applied to a diagnostic support apparatus for performing diagnosis support for a user using the medical image. The present invention can also be applied to a medical service support apparatus for supporting the medical service, such as a diagnostic report, using the medical image.

Figure 15:
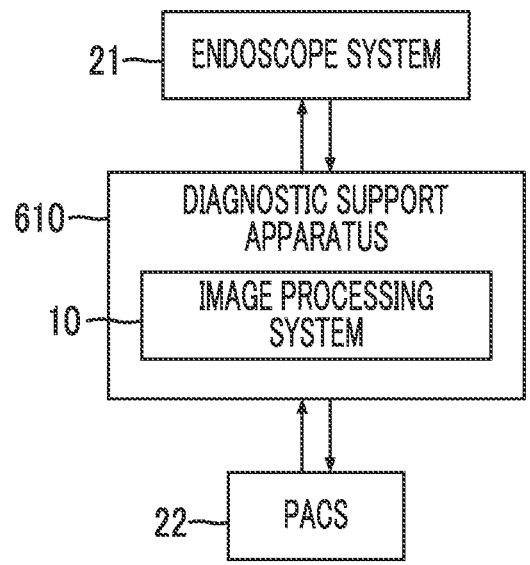
FIG. 15 is a diagnostic support apparatus including the image processing system.
Figure 16:
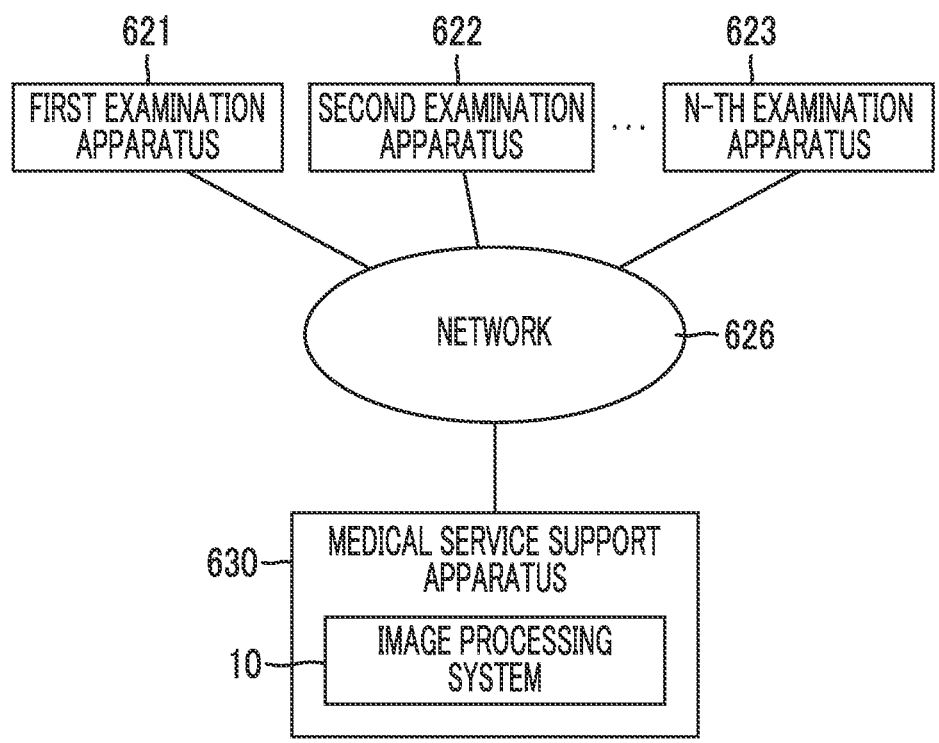
FIG. 16 is a medical service support apparatus including the image processing system.

For example, as shown in FIG. 15, a diagnostic support apparatus 610 is used in combination with a modality such as an image processing system 10 and a PACS 22. As shown in FIG. 16, a medical service support apparatus 630 is connected to various examination apparatuses such as a first medical image processing system 621, a second medical image processing system 622, . . . , and an N-th medical image processing system 623 through a certain network 626. The medical service support apparatus 630 receives medical images from the first to N-th medical image processing systems 621, 622, . . . , and 623, and supports the medical service on the basis of the received medical images.

In the above embodiment and modification examples, hardware structures of processing units for executing various kinds of processing, such as the medical image acquisition unit 11, the medical image analysis processing unit 12, each unit forming the medical image analysis processing unit 12, the display control unit 15, the input receiving unit 16, the overall control unit 17, the medical image acquisition unit 35, the medical image analysis processing unit 36, the display control unit 37, the effective region setting unit 40, the feature amount calculation unit 42, the second region integration unit 43, the stage determination unit 44, the distribution index value calculation unit 44a, the determination unit 44b, and the first region integration unit 44c, are various processors shown below. The various processors include a central processing unit (CPU) that is a general-purpose processor that functions as various processing units by executing software (program), a programmable logic device (PLD) that is a processor whose circuit configuration can be changed after manufacture, such as field programmable gate array (FPGA), a dedicated electrical circuit that is a processor having a circuit configuration designed exclusively for executing various types of processing, a graphical processing unit (GPU), and the like.

One processing unit may be configured by one of various processors, or may be configured by a combination of the same or different kinds of two or more processors (for example, a combination of a plurality of FPGAs, a combination of a CPU and an FPGA, or a combination of a CPU and a GPU). In addition, a plurality of processing units may be configured by one processor. As an example of configuring a plurality of processing units by one processor, first, as represented by a computer, such as a client or a server, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by using one or more of the above-described various processors as hardware structures.

More specifically, the hardware structure of these various processors is an electrical circuit (circuitry) in the form of a combination of circuit elements, such as semiconductor elements. The hardware structure of the storage unit is a storage device such as a hard disc drive (HDD) or a solid state drive (SSD).

The present invention can also be implemented by the following alternative embodiment.

A processor device is provided. The processor device is configured to:

acquire a medical image obtained by imaging an observation target;
calculate a feature amount of the observation target for each of pixels of an image region of the medical image or for each of divided regions obtained by dividing the image region of the medical image into a specific size; and
determine a disease stage of the observation target by using a spatial distribution of the feature amount.

EXPLANATION OF REFERENCES

10: image processing system
11: medical image acquisition unit
12: medical image analysis processing unit
13: display unit
15: display control unit
16: input receiving unit
17: overall control unit
18: saving unit
21: endoscope system
22: PACS
31: endoscope
32: light source device
33: processor device
34: monitor
35: medical image acquisition unit
36: medical image analysis processing unit
37: display control unit
40: effective region setting unit
42: feature amount calculation unit
43: second region integration unit
44: stage determination unit
44a: distribution index value calculation unit
44b: determination unit
44c: first region integration unit
46: dark area
48: edge
50: specular reflection
610: diagnostic support apparatus
621: first examination apparatus
622: second examination apparatus
623: N-th examination apparatus
626: network
630: medical service support apparatus
RP: image region
Rx: effective region
P: divided region
P1, P2, Pn, Ps, Pt, Pu, Pv, Pw: divided region
Pa, Pb, Pc, Pd, Pf: divided region (abnormal region)
IR1, IR2, IR3: integrated abnormal region
IRx: integrated region

What is claimed is:

1. A medical image processing system comprising:
a processor configured to:
   acquire a medical image obtained by imaging an observation target;
   calculate a feature amount of the observation target for each of pixels of an image region of the medical image or for each of divided regions obtained by dividing the image region of the medical image into a specific size;
   determine a disease stage of the observation target by using a spatial distribution of the feature amount;
   calculate a distribution index value which is an index value of the spatial distribution of the feature amount; and
   determine the disease stage based on the distribution index value,
wherein the distribution index value is a variance of the feature amount,
the disease stage is an early stage and a progress staged,
a variation in the spatial distribution of the feature amount in the progress stage is larger than a variation in the spatial distribution of the feature amount in the early stage, and
a degree of progress of the disease stage increases as the variance of the feature amount increases.

2. The medical image processing system according to claim 1,
wherein the distribution index value is an index value related to a spatial distribution of an abnormal region indicating a pixel or a divided region where the feature amount is outside a specific range.

3. The medical image processing system according to claim 2,
wherein the index value related to the spatial distribution of the abnormal region is at least one of the number or an area of the abnormal regions or a ratio occupied by the abnormal region in the image region, and
a degree of progress of the disease stage increases as the number or the area of the abnormal regions or the ratio of the abnormal region increases.

4. The medical image processing system according to claim 1,
wherein the processor is configured to integrate abnormal regions indicating a pixel or a divided region where the feature amount is outside a specific range, and
the distribution index value is an index value related to a spatial distribution of a specific integrated abnormal region that satisfies a specific condition among integrated abnormal regions in which the abnormal regions are integrated.

5. The medical image processing system according to claim 1, wherein the processor is further configured to:
   integrate adjacent pixels or divided regions in a case where a feature amount of the adjacent pixels or divided regions is within a feature amount range,
   wherein the distribution index value is an index value related to a spatial distribution of an integrated region in which the adjacent pixels or divided regions are integrated.

6. The medical image processing system according to claim 1,
wherein the feature amount is at least one of a blood vessel density, a blood vessel contrast, change in a blood vessel width, or an average value of the blood vessel width.

7. The medical image processing system according to claim 1,
wherein the processor is configured to calculate different types of a plurality of calculation feature amounts for each pixel or for each divided region, and calculate a first calculation value obtained by calculation based on the plurality of calculation feature amounts, as the feature amount.

8. The medical image processing system according to claim 7,
wherein the calculation feature amount is a blood vessel density of a first layer blood vessel and a blood vessel density of a second layer blood vessel different from the first layer blood vessel, and the first calculation value is a ratio of the blood vessel density of the first layer blood vessel to the blood vessel density of the second layer blood vessel.

9. The medical image processing system according to claim 1,
wherein the processor is configured to calculate different types of a plurality of calculation feature amounts for each pixel or for each divided region,
calculate a calculation distribution index value which is an index value of a spatial distribution of each of the calculation feature amounts, and calculate a second calculation value obtained by calculation based on the calculation distribution index value, as a distribution index value, and
determine the disease stage based on the distribution index value.

10. The medical image processing system according to claim 1, wherein the processor is further configured to:
set an effective region in which the disease stage is determinable in the image region, and
calculate the feature amount for each divided region in the effective region.

11. The medical image processing system according to claim 1,
wherein, in a case of calculating the feature amount for each pixel, the processor is configured to calculate a feature amount of a specific region, which is obtained from the specific region including the pixel, as the feature amount for each pixel.

12. A medical image processing system comprising:
a processor configured to:
acquire a medical image obtained by imaging an observation target;
calculate a feature amount of the observation target for each of pixels of an image region of the medical image or for each of divided regions obtained by dividing the image region of the medical image into a specific size;
determine a disease stage of the observation target by using a spatial distribution of the feature amount;
calculate a distribution index value which is an index value of the spatial distribution of the feature amount;
determine the disease stage based on the distribution index value; and
integrate abnormal regions indicating a pixel or a divided region where the feature amount is outside a specific range,
among integrated abnormal regions in which the abnormal regions are integrated, the integrated abnormal region whose area is equal to or larger than a certain value is set as a specific integrated abnormal region, and the integrated abnormal region whose area is less than the certain value is not set as the specific integrated abnormal region,
the distribution index value is an index value related to a spatial distribution of the specific integrated abnormal region,
the distribution index value is a variance of the feature amount, and
a degree of progress of the disease stage increases as the variance of the feature amount increases.

* * * * *